(12) United States Patent
Clark et al.

(10) Patent No.: US 7,247,491 B2
(45) Date of Patent: Jul. 24, 2007

(54) METHOD FOR DETERMINING RELEASE OF A PEPTIDE FROM A SUSTAINED RELEASE POLYLACTIDE FORMULATION

(75) Inventors: Brian Collingwood Clark, Cheshire (GB); David Michael Cross, Cheshire (GB); Paul Richard Gellert, Cheshire (GB); Rodney Simon Kittlety, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 534 days.

(21) Appl. No.: 10/398,791

(22) PCT Filed: Oct. 5, 2001

(86) PCT No.: PCT/GB01/04439

§ 371 (c)(1),
(2), (4) Date: Apr. 8, 2003

(87) PCT Pub. No.: WO02/30391

PCT Pub. Date: Apr. 18, 2002

(65) Prior Publication Data

US 2004/0092452 A1     May 13, 2004

(30) Foreign Application Priority Data

Oct. 11, 2000   (GB) .................................. 0024884.9

(51) Int. Cl.
*G01N 33/00*     (2006.01)

(52) U.S. Cl. .......................... 436/86; 424/457; 424/468
(58) Field of Classification Search .................. 436/86; 424/457, 468
See application file for complete search history.

(56) References Cited

U.S. PATENT DOCUMENTS 5,702,716 A   12/1997   Dunn et al.
5,736,152 A    4/1998   Dunn

OTHER PUBLICATIONS

Herrmann et al., "Biodegradable, somatostatin acetate containing microspheres prepared by various aqueous and non-aqueous solvent evaporation methods," European Journal of Pharmaceutics and Biopharmaceutics 45:75-82 (1998).
McDaniel, "In vitro and in vivo release of pulsitile microsphere formulations," Proceed. Int'l. Symp. Control Rel. Bioact. Mater., 25:443-444 (1998).
Shameem et al., "A short-term (accelerated release) approach to evaluate peptide release from PLGA depot formulations," AAPS Pharmsci 1(3):1-12 (1999).

*Primary Examiner*—Jill Warden (57) ABSTRACT

A method for determining the release of a peptide from a sustained release polylactide formulation which can be carried out in a shorter time than a real-time method by accelerating the release of the peptide from the formulation. It can be used to discriminate between batches of formulations for quality control purposes and to discriminate between formulations, for example, having different drug loadings.

11 Claims, 6 Drawing Sheets

METHOD FOR DETERMINING RELEASE OF A PEPTIDE FROM A SUSTAINED RELEASE POLYLACTIDE FORMULATION

This application is a national stage filing under 35 U.S.C. 371 of International Application No. PCT/GB01/04439, filed Oct. 5, 2001, which claims priority from United Kingdom Application No. 0024884.9, filed Oct. 11, 2000, the specifications of each of which are incorporated by reference herein. International Application No. PCT/GB01/04439 was published under PCT Article 21(2) in English.

The present invention relates to an accelerated method for determining the release of a peptide from a sustained release polylactide formulation.

The therapeutic effectiveness of pharmaceutically active drugs such as peptides may depend on their continued release over a prolonged period of time. It is recognised that a single administration of a pharmaceutical composition, comprising such a drug, which results in release of the drug over an extended period of time, for example one month or more, has significant clinical advantages, for example avoiding the need for repeated administrations. Such extended or sustained release can be achieved by administering the drug in the form of a biodegradable polymer matrix which releases the drug over a prolonged period. Suitable biodegradable polymers are polylactides. The term 'polylactide' is used in a generic sense to include polymers of lactic acid alone, copolymers of lactic and glycolic acid, mixtures of such polymers, mixtures of such copolymers and mixtures of such polymers and copolymers, the lactic acid being either in racemic or optically active form.

The polylactide polymer may be prepared using known methods. Suitable techniques include, but are not limited to, condensation polymerisation of the appropriate hydroxy acids, i.e. lactic and glycolic acids, and ring opening polymerisation of the appropriate lactide and glycolide dimers.

Examples of peptides which are beneficially administered in a sustained release formulation include LHRH analogues which can be used in the treatment of a number of diseases and clinical disorders. An example of one such disease is prostate cancer, a sex hormone dependent cancer. This can be treated by chemical means by interfering with the production of luteinising hormone (LH) which regulates the synthesis of male hormones. Luteinising hormone releasing hormone (LHRH) is a natural hormone, produced by the hypothalamus, that interacts with the luteinising hormone releasing hormone receptor in the pituitary to stimulate the production of LH. Administration of an LHRH analogue will disturb the production of the LH. Such LHRH analogues have similarly been used to treat, for example, estrogen-dependent cancers such as breast cancer. Examples of such LHRH analogues include, for example, leuprorelin (U.S. Pat. No. 4,005,063), goserelin (U.S. Pat. No. 4,100,274), triptorelin (U.S. Pat. No. 4,010,125) and buserelin (U.S. Pat. No. 4,024,248).

Examples of commercially available LHRH analogues include 'Zoladex', which contains goserelin as the active ingredient, and 'Prostap 3', which contain leuprorelin as the active ingredient.

Another class of peptide derivatives which are beneficially administered in a sustained release formulation include Sandostatin, a commercially available form of octreotide and Somatuline, a commercially available form of lanreotide, both of which are somatostatin analogues.

Another class of peptide derivatives which possess pharmacologically beneficial properties which can be used in treating autoimmune diseases or medical conditions, such as rheumatoid arthritis and other MHC class II dependent T-cell mediated diseases and which may usefully be administered from a sustained release composition are those compounds described in WO 97/31023, published 28 Aug. 1997, incorporated herein by reference.

Whilst real-time in-vivo release studies are essential to evaluate sustained release compositions, a discriminatory in-vitro method is essential to evaluate differences between batches for quality control purposes. Whilst such in-vitro methods are typically real time tests typically performed at 37° C., it is advantageous if an accelerated method can be applied to confirm the quality of clinical trials materials or marketed products. The results of the test would be compared with specification limits, typically at three or more time-points, chosen to ensure that all batches released will be effective in terms of onset, maintenance and duration of action. Such an accelerated in-vitro method may also be used in product development, to evaluate the effect of modifications to composition or manufacturing process, thus shortening development time-lines and minimising the need for in-vivo studies. An important aspect is to ensure that complete release of the peptide is achieved during the duration of the accelerated method. By 'complete release' is meant that at least 90%, preferably 95% or more, of the peptide is released during the duration of the test. Another important feature is to ensure that the short-term or accelerated release correlates with real-time release, i.e. similar release profiles of drug from the formulation are achieved, in order that the short-term release can be used as predictive of real-time release. By 'similar-release profiles' is meant the release profile from the real-time and accelerated tests are essentially the same shape. For example, if the release profile from the real-time method is consistent with, for example, two-phase release the release profile from the accelerated method should also show two phases of release. The use of such an accelerated method may mean in the case of a three month sustained release formulation, that individual formulations could be compared after a matter of a few days rather than waiting for a real-time analysis taking around 90 days.

Such accelerated methods have previously been described. For example, McDaniel, Proceed. Int'l. Symp. Control. Rel. Bioact. Mater., 25, 1998, p 443, have disclosed an accelerated in-vitro release method for microsphere formulations containing a water-insoluble analogue of the avermectin family of antibiotics in a polylactide glycolide polymer matrix. This method employs one of a range of organic amines as catalysts to accelerate degradation of the polymer. The use of high temperatures, approaching the glass transition temperature (Tg) of the polymer, to further accelerate degradation of the polymer was rejected.

Shameem et al in AAPS Pharmsci 1999, 1(3), article 7 describes an accelerated method to evaluate peptides from polylactide glycolide microsphere formulations. In this method it was found necessary to use temperatures which were above the Tg of the polymer to ensure complete release of the peptide. The dissolution medium was optimised at pH 4 and polyvinylalcohol was present as a surfactant to prevent the microspheres from sticking together. Complete release of the peptide was typically achieved in the accelerated test within 30 to 40 hours whereas real-time release was 28 days.

The methods disclosed in these references lead in two opposed directions since one teaches the use of the temperatures above the Tg of the polymer whereas the other teaches temperatures below the Tg of the polymer to ensure accelerated degradation of the polymer. Furthermore, neither reference identifies an accelerated test for a 1 month formulation which gives complete release of the peptide and can be carried out in less than 30 hours. Clearly, it is advantageous if the accelerated method can be carried out in 15 hours or less and preferably 12 hours or less since it enables the test to be complete within slightly extended working day.

Thus, according to the invention there is provided a method for determining the release of a peptide from a sustained release polylactide formulation, which can be carried out in a shorter time than a real-time method by accelerating the release of the peptide from the formulation, the method comprising i) adding the formulation to a fixed amount of dissolution medium, the dissolution medium having an osmolarity in the range 100 to 550 mOsmol/L and pH in the range 7 to 12, and, optionally, comprising one or more further components selected from catalysts and surfactants;

ii) maintaining the temperature of the dissolution medium within the range 0 to 50° C. above the Tg of the polylactide polymer; and iii) determining the amount of peptide in the sample, the osmolarity, pH and temperature being chosen such that the accelerated release profile is similar to the real-time release profile.

The method can be used to discriminate between batches of formulations for quality control purposes and or to discriminate between formulations, for example, those having different drug loadings or being formed from different polymers.

Preferably, the dissolution medium will be sampled at regular time intervals, such as for example, at hourly time intervals.

The sustained release formulation may be in the form of a solid composition which may be administered to patients by subdermal implantation or by injection or in the form of a suspension for injection comprising microparticles or microcapsules. Such compositions are described in, amongst other references, European Patents 58 481 and 52 510, which are incorporated herein by reference. When the formulation is in the form of a suspension for injection, the dissolution medium will preferably additionally include a surfactant which assists in preventing agglomeration of the microparticles or microcapsules which may occur, particularly at higher temperatures. The use of a surfactant can, however, also be advantageously added to the dissolution medium when solid compositions are being tested. Suitable surfactants include polyvinyl alcohol, sodium dodecyl sulphate and Polysorbate 80 (polyoxyethylene sorbitan monooleate). The surfactant, if present, is preferably included at a level up to 0.5 and, in particular, from 0.05 to 0.5% by weight. The accelerated method is particularly suitable for monolithic implants also known as monolithic depot formulations of the type described in EP 58 481.

The accelerated method is particularly suitable for formulations in which the polylactide is a lactide glycolide copolymer having a lactide to glycolide ratio in the range 1:1 to 19:1 and an average molecular weight in the range between 10 and 150 kDa and where the drug loading is between 3 and 30% by weight, preferably between 8 and 30% by weight.

In one embodiment of the method according to the invention, the dissolution medium is sampled whilst the volume of the dissolution medium is maintained at constant volume.

Thus, according to a further aspect of the invention there is provided a method for determining the release of a peptide from a sustained release polylactide formulation, which can be carried out in a shorter time than a real-time method by accelerating the release of the peptide from the formulation, the method comprising i) adding the formulation to a fixed amount of dissolution medium, the dissolution medium having an osmolarity in the range 200 to 500 mOsmol/L, pH in the range 7 to 12 and, optionally, comprising a catalyst such as an organic amine;

ii) maintaining the temperature of the dissolution medium within the range 0 to 50° C. above the Tg of the polylactide polymer;

iii) sampling the dissolution medium whilst maintaining the volume of the dissolution medium constant; and iv) determining the amount of peptide in the sample, the osmolarity, pH and temperature being chosen such that the accelerated release profile is similar to the real-time release profile.

The osmolarity, pH and temperature of the dissolution medium will depend on the nature of the formulation being tested. For any particular formulation, initially it is necessary to establish an in-vivo release profile ideally in humans but often using an animal model (rat, dog or other species as considered appropriate for the indication. Such a profile will typically be based on pharmacokinetic data derived from monitoring the concentration of the active ingredient in blood over a period exceeding the anticipated duration of release from the product). Alternatively a real time in-vitro dissolution test can be used to obtain a real-time release profile. The conditions for an accelerated method can then be established by varying the osmolarity, pH and temperature of the dissolution medium within the ranges hereinbefore defined until the release profile from the accelerated method is similar to the real-time release profile and the duration of the method is acceptable. Formulations and or manufacturing conditions may be modified and the effect of such modifications assessed in-vitro using the accelerated test, thus minimising the need for real time in-vivo studies. As stated above, it is advantageous if the conditions can be chosen such that the duration of the test is complete within a working day, particularly if the dissolution medium is sampled manually. Furthermore, if the method is being used for rank correlation of clinical batches it is important that this can be completed in as short a time as possible since ultimately this may reduce the delay between batch production and release of product into the market.

Preferably, release of the peptide from a 1 month sustained release formulation will be accelerated to be complete in less than 12 hours. For three and six month sustained release formulations the accelerated method will preferably aim to give complete release of the peptide within less than 25 hours and 50 hours respectively.

Preferably the peptide is an LHRH analogue, octreotide, lanreotide or a MHC class II antagonist. Most preferably the peptide is goserelin or an MHC class II antagonist.

As stated above, for the accelerated method to be useful it is important that the release profile using the accelerated method is similar to that obtained using the real-time method. Whilst we have found that increasing the temperature at which the method is carried out to temperatures greater than 50° C. above the Tg of the polymer may lead to a faster release of peptide, such high temperatures may result in a loss of the integrity and physical form of the formulation which is likely to affect the release profile. Preferably the temperature of the dissolution medium will be in the range 5 to 30° C., more preferably 10 to 30° C., most preferably 10 to 25° C. above the Tg of the polymer.

Suitable catalysts are organic amines which are preferably selected from piperidine, n-methylpiperidine and piperazine. Piperidine is particularly preferred. The organic amine, if present, is preferably present in an amount up to 1% by weight, suitably from 0.1 to 1% by weight.

The dissolution medium comprises a buffer system suitable to maintain the pH at the desired value. Preferably the pH of the dissolution medium will be in the range greater than pH 7, such as pH 7.4, to pH 12 and more preferably pH 8 to pH 11. An ionic strength adjuster, typically sodium chloride, may also be present to ensure the osmolarity of the dissolution medium is maintained at a suitable level. Osmolarity of the dissolution medium may be determined by the method described for ideal osmolar concentration in the US Pharmacopoeia. Preferably the osmolarity will be in the range 280 to 500 mOsmol/L, most preferably 400 to 500 mOsmo/L.

In one embodiment, the method can be operated manually by adding the formulation to be tested into a vessel containing the dissolution medium. The temperature of the vessel and its contents can be maintained by placing it in, for example, a water bath. At regular intervals, for example, at hourly intervals, an aliquot of dissolution medium is removed from the vessel and replaced with fresh dissolution medium so that the total volume remains constant.

The absorbance of the sample can be measured using a UV spectrophotometer.

The % dissolution at the particular time interval is calculated as follows:—

The absorbance of sample solutions $n_1, n_2, n_3, \ldots n_r \ldots n_x$ is $A_1, A_2, A_3 \ldots A_r \ldots A_x$ where $n_r$ is before $n_x$ and $A_r$ is absorbance at time point $n_r$ which is earlier than $n_x$.

$$\% \text{ dissolution} = \frac{\left[(A_x \times F \times V_M) + V_S F \sum_{r=1}^{r=x-1} Ar\right] \times 100}{W_p}$$

where,

% dissolution is the cumulative percentage of nominal drug content release by time point x F=Absorbance of 1 mg of the active in 1 ml of dissolution medium $W_p$=Nominal content, in mg, of the drug in the formulation being tested Ax=Absorbance at time point $n_x$ Ar=Absorbance at time point $n_r$ which is earlier than $n_x$ $V_M$=total volume of the dissolution medium $V_S$=sample volume In an alternative embodiment, the manual operation can be replaced by the use of commercially available equipment which relies on the use of a flow cell such as USP Apparatus IV, commercially available from Sotax or Erweka, and as described in United States Pharmacopeia 23<724>Drug Release.

In the Figures

The invention will now be illustrated by reference to the following non-limiting examples.

EXAMPLES

Example 1

A commercially available sample of 'Zoladex' 3.6 mg (which contains goserelin acetate in a polylactide glycolide copolymer) was used in this example. The real-time dissolution of this sample was measured using an in vitro real-time test.

The accelerated method conditions for a sample of 'Zoladex' 3.6 mg were determined. The buffer used to maintain the pH at the required level of 8.0 comprised citric acid, boric acid, phosphoric acid and sodium hydroxide. Piperidine (4 ml) was added to catalyse release of the peptide from the polymer matrix.

The osmolarity was determined to be 500 mOsMol/l and the temperature was 65° C. which is approximately 23° C. above the Tg of the polymer.

Figure 1:
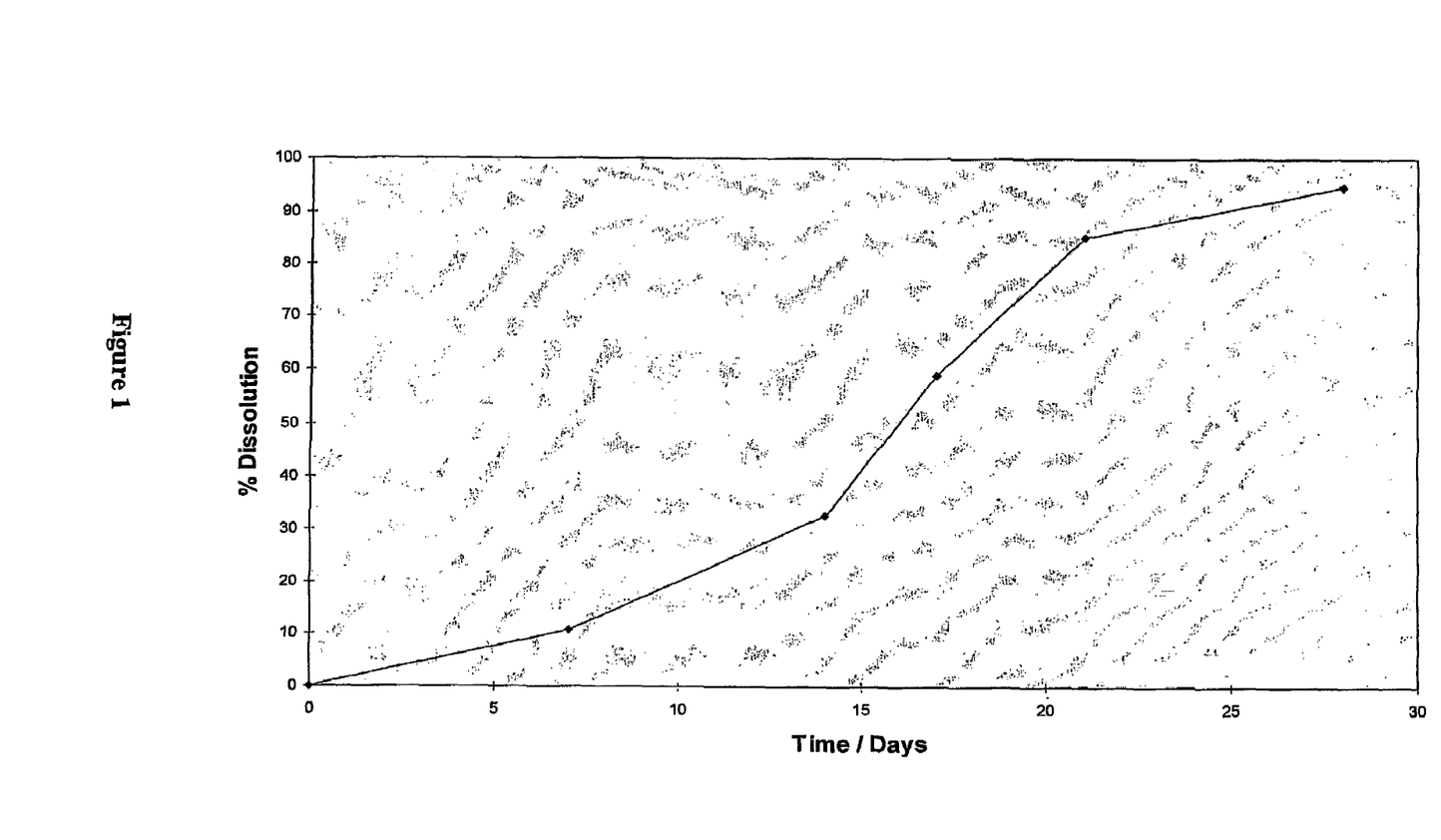
FIG. 1 is a plot of the real-time release profile of a formulation showing % dissolution of drug in the dissolution medium release versus time.
Figure 2:
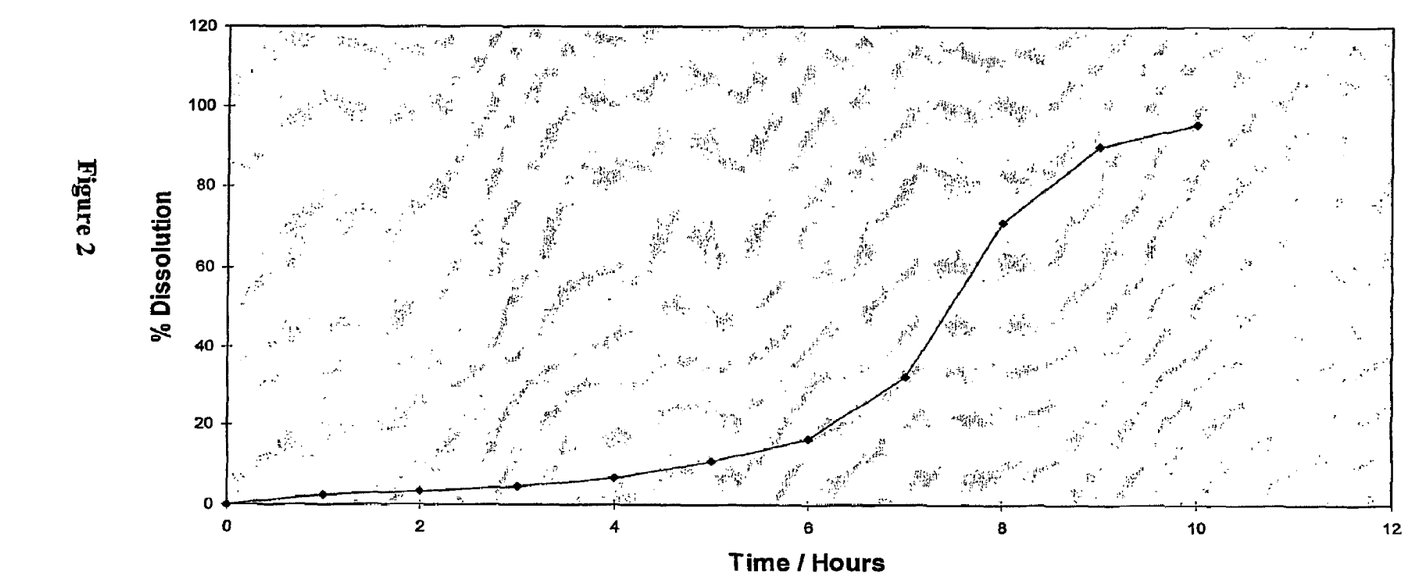
FIG. 2 is a plot of the accelerated release profile of a formulation showing % dissolution of drug in the dissolution medium release versus time.

FIG. 2 shows that complete release occurs in 10 hours.

'Zoladex' is a Trade Mark of the AstraZeneca group of companies.

Zoladex 3.6 mg is a one month duration of action monolithic depot formulation. Zoladex 10.8 mg is a three month duration of action monolithic depot formulation.

Example 2

Figure 3:
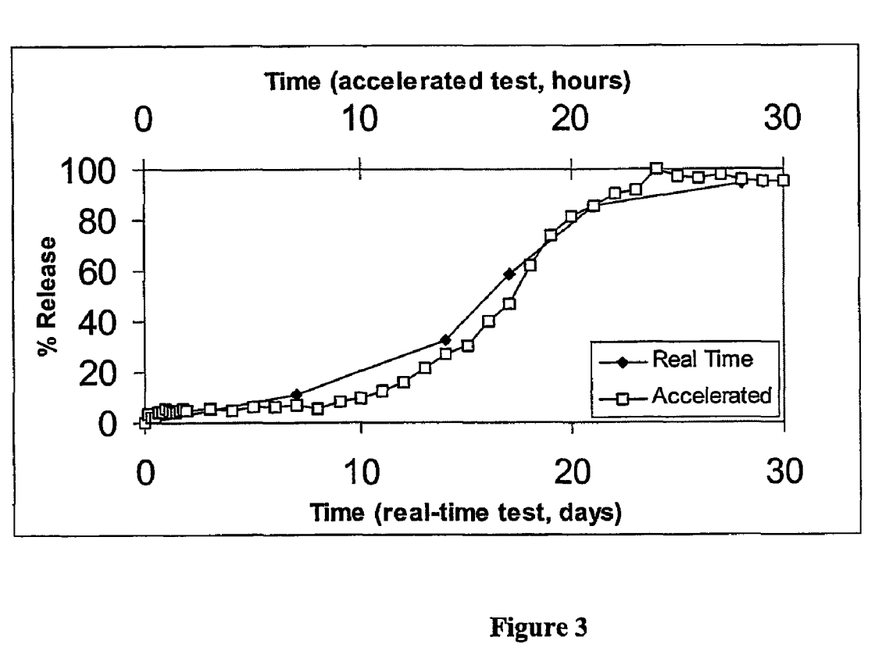
FIG. 3 is a plot comparing the release profiles for Zoladex 3.6 mg depot obtained for a real-time in-vitro dissolution test against that for an accelerated release test.

A further experiment was carried out with another sample of 'Zoladex' 3.6 mg. In this example, the pH was maintained at pH 7.4 using a buffer comprising potassium dihydrophosphate, disodium orthophosphate and sodium chloride. Sodium dodecyl sulphate were also added. The osmolarity was determined to be 500 mOsMol/l and the temperature was 65° C. which is approximately 23° C. above the Tg of the polymer. The results comparing the release profile for Zoladex 3.6 mg depot under the conditions of the real-time in vitro dissolution test with that obtained for the accelerated release test are as shown in FIG. 3.

Example 3

The relationship between duration of action and rate of release in the accelerated release test has been investigated for the marketed products Zoladex 3.6 mg and Zoladex 10.8 mg. An experimental Zoladex formulation of 6-months duration made as described below and an experimental monolithic depot formulation of the experimental MHC Class II antagonist as described in WO 97/31023 have also been studied.

The 6 month goserelin containing formulation was prepared by melt extrusion of a freeze-dried mixture of drug and polymer. Batch sizes of 5 grams were prepared by dissolving 1.16 grams of goserelin acetate and 3.84 grams of a 46.2 kDa poly(dl lactide) in glacial acetic acid and drop freezing into liquid nitrogen. The resulting frozen spheroids were freeze dried for approximately 24 hours using a freeze dryer (Edwards), to remove glacial acetic acid from the samples. The resulting solid was then put through a secondary drying step as follows. Temperature was ramped from 20° C. from 45° C. over an hour followed by dwell time of 5 hours. Temperature was then ramped again over 1 hour from 45° C. to 60° C. and then held at 60° C. for a period of 5 hours. Samples were retained in a vacuum dessicator prior to extrusion. The drug/polymer blend prepared in this manner was extruded using a one gram capacity, stainless steel extruder consisting of a barrel/nozzle, base and die with a nozzle diameter of 2.3 mm. The extruder was heated using a pipe clamp, the temperature of which was controlled through a feedback circuit containing a thermocouple, located in thermal contact with the extruder barrel, and a custom built controller unit. Pressure was applied to the extruder die via a standard hydraulic KBr Press (Specac). Extrusion pressure was controlled manually. The temperature of the extruder was initially raised to 95° C. over a period of 60 minutes, and then held at this temperature for a further 120 minutes. Extrusion of the drug/polymer melt was then performed by applying a pressure of approximately 1 ton to the extruder die. The resulting extrudate was cut into the required lengths for dissolution testing.

The conditions for this experiment of this example were chosen so that release from the Zoladex 3.6 mg depot was complete in approximately 3 hours.

Figure 4:
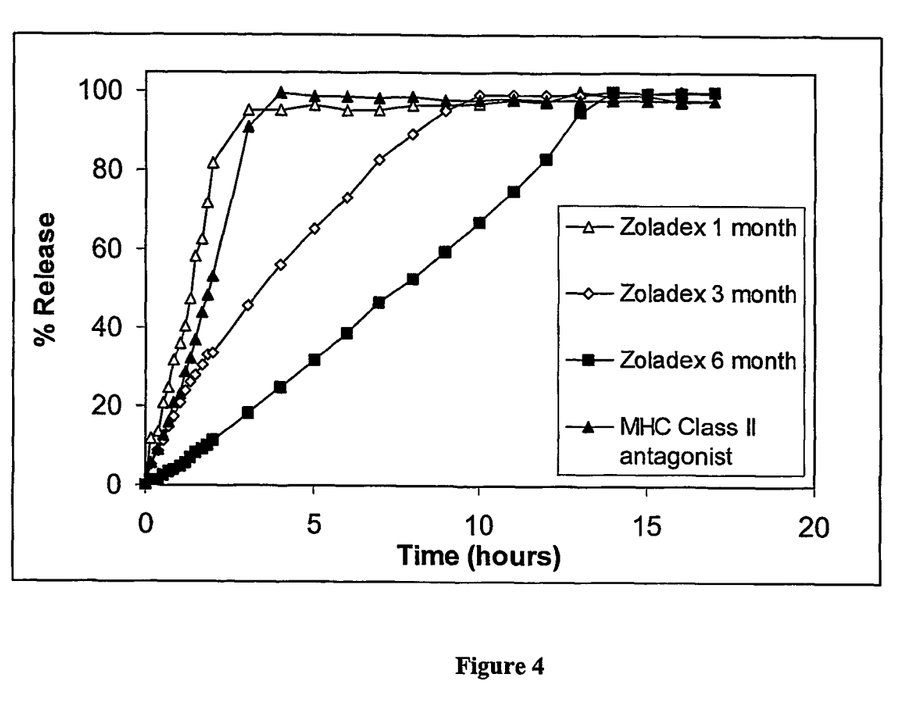
FIG. 4 is a plot showing accelerated release profiles for a number of different monolithic depot formulations.

The buffer used to maintain the pH comprised citric acid, boric acid, phosphoric acid and sodium hydroxide. The resulting accelerated release profiles are presented in FIG. 4.

Figure 5:
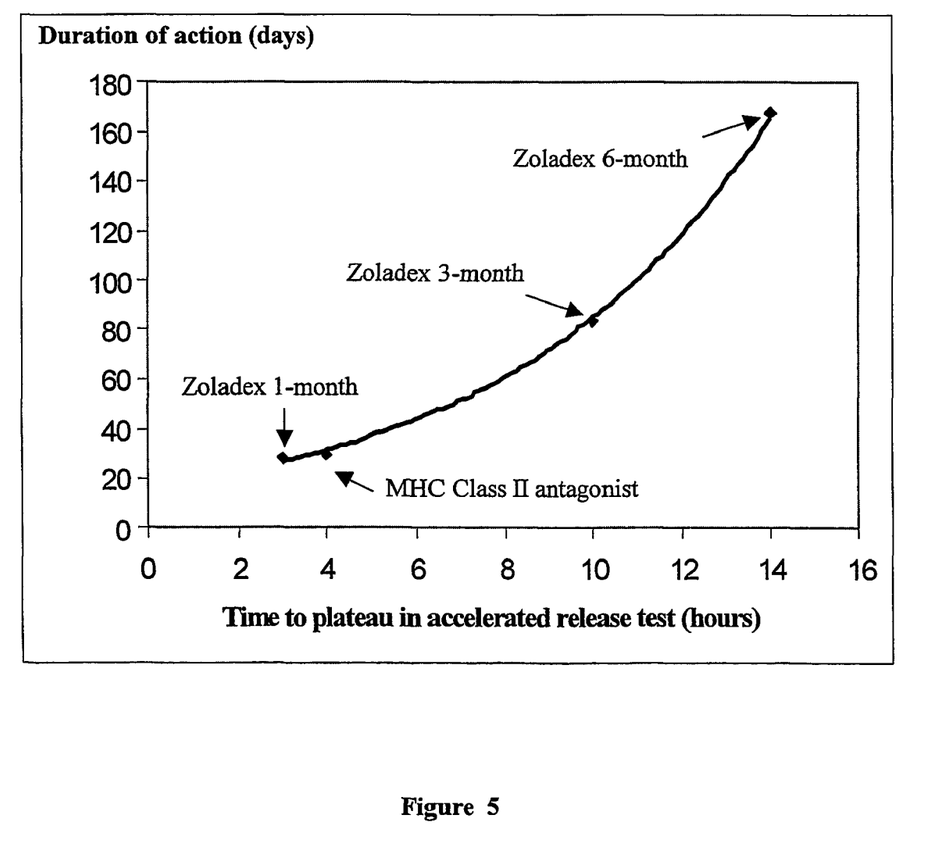
FIG. 5 is a plot showing the relationship between the duration of action and time to plateau for the different monolithic depot formulations shown in FIG. 4.

It is apparent that under these conditions release occurs more rapidly for the products of shorter duration. The relationship between duration of action and time to plateau (complete release) in the accelerated release test is shown in FIG. 5.

The ability to rapidly assess duration of action may be of benefit in formulation optimisation studies in allowing the preliminary screening of trial formulations prior to proof of concept in animal or human models.

Example 4

In this example an accelerated release profile was measured for Zoladex 10.8 mg and compared with an accelerated release profile for Prostap 3, a 3 month duration of action commercially available microparticulate formulation containing leuprorelin as the active component. The experiments were carried out at pH 12. The buffer used to maintain the pH at the required level of 8.0 comprised citric acid, boric acid, phosphoric acid and sodium hydroxide. The osmolarity was determined to be 200 mOsMol/l and the temperature was 65° C.

Figure 6:
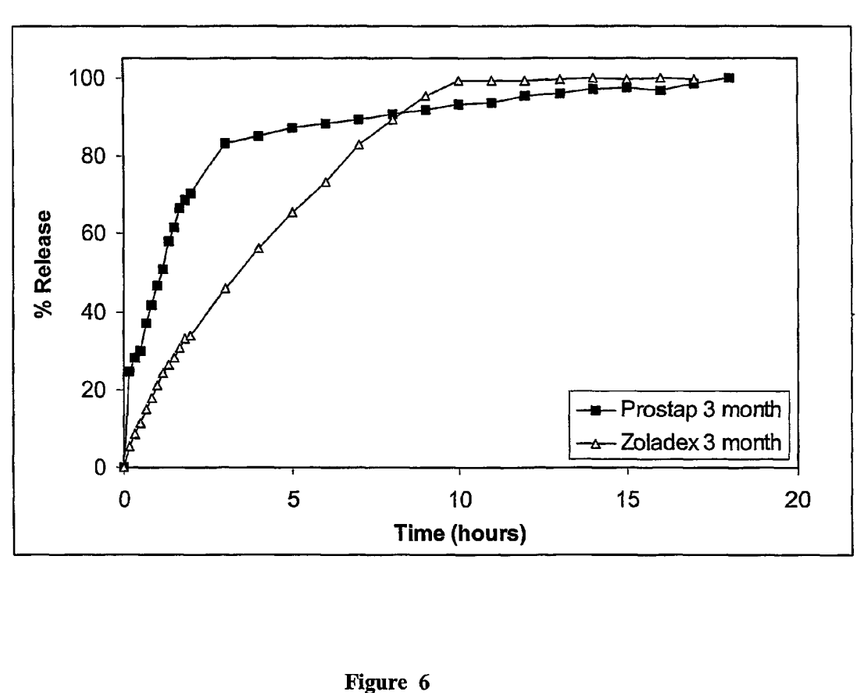
FIG. 6 is a plot comparing the accelerated release profile for a 3 month microsphere formulation with Zoladex 10.8 mg.

The results are shown in FIG. 6 and confirm that the accelerated release method is applicable to microparticulate as well as monolithic depot formulations.

The invention claimed is:

1. A method for determining the real-time release of a peptide from a sustained release polylactide formulation said formulation comprising a polylactide polymer and the peptide, which method is carried out in a shorter time than a real-time method by accelerating the release of the peptide from the formulation, the method comprising
    i) adding the formulation to a fixed amount of dissolution medium, the dissolution medium having an osmolarity in the range of 100 to 550 mOsmol/L and pH in the range 7 to 12;
    ii) maintaining the temperature of the dissolution medium within a range of 0 to 50° C. above the Tg of the polylactide polymer; and
    iii) determining the amount of the peptide left in the formulation at three or more time points to establish an accelerated release profile, the osmolarity, the pH and the temperature of the dissolution medium being chosen within the ranges provided in i), and correlating the accelerated release profile of the peptide from the formulation to the real-time release profile of the peptide from the formulation.

2. A method according to claim 1 wherein the dissolution medium further comprises one or more additives selected from catalysts and surfactants.

3. A method according to claim 1 wherein the osmolarity of the dissolution medium is in the range 280 to 500 mOsmol/L.

4. A method according to claim 2 wherein the osmolarity of the dissolution medium is in the range 280 to 500 mOsmol/L.

5. A method according to claim 1 wherein the pH of the dissolution medium is in the range 7.4 to 12.

6. A method according to claim 1 wherein the temperature of the dissolution medium Is maintained within the range 10 to 30° C. above the Tg of the polylactide polymer.

7. A method according to claim 1 wherein the peptide is selected from LHRH analogues, somatostatin analogues and a peptide MHC class II antagonist.

8. A method according to claim 1 wherein the peptide is an LHRH analogue.

9. A method according claim 1 wherein the peptide is goserelin.

10. A method according to claim 1 wherein the method comprises sampling the dissolution medium whilst maintaining the volume thereof constant.

11. A method according to claim 1 wherein the sustained release formulation is in the form of a monolithic depot formulation.

* * * * *